United States Patent [19]
Ferrari

[11] 3,973,027
[45] Aug. 3, 1976

[54] ANALGESIC METHOD CONTAINING LYSINE 2-(2-METHYL-3-CHORO-ANILINO)-3-NICOTINATE

[75] Inventor: Pier Nello Ferrari, Buenos Aires, Argentina

[73] Assignee: Roemmers Sociedad Anonima Industrial, Comercial y Financiera, Buenos Aires, Argentina

[22] Filed: Oct. 15, 1974

[21] Appl. No.: 515,065

[30] Foreign Application Priority Data
Mar. 7, 1974 France .......................... 74.07817

[52] U.S. Cl. ............................... 424/266; 424/14
[51] Int. Cl.² ...................................... A61K 31/455
[58] Field of Search .................................. 424/266

[56] References Cited
UNITED STATES PATENTS
3,172,812   3/1965   Halpern ..................... 424/316 X FOREIGN PATENTS OR APPLICATIONS
790,749     2/1973   Belgium ........................ 424/266
1,596,106   7/1970   France ........................... 424/266
925,567     5/1963   United Kingdom ................ 424/266

*Primary Examiner*—Dale R. Ore
*Attorney, Agent, or Firm*—Holman & Stern

[57] ABSTRACT

Novel analgesic pharmaceutical compositions are disclosed, wherein the active principle is Lysine 2-(2-methyl-3-chloro-anilino)-3-nicotinate. The recommended dosage unit is from 10 to 500 milligrams of the active ingredient. The analgesic activity of the compound according to the invention is more than 20 times more intense than that of acetylsalicylic acid, taken as the unitary reference.

6 Claims, No Drawings

ANALGESIC METHOD CONTAINING LYSINE 2-(2-METHYL-3-CHLORO-ANILINO)-3-NICOTINATE

This invention relates to Lysine 2-(2-methyl-3-chloro-anilino)-3-nicotinate, having the formula:

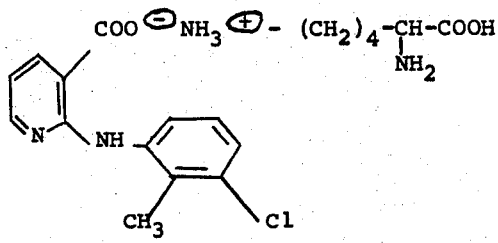

More specifically, the present invention relates to pharmaceutical compositions having an analgesic action and containing, as the active ingredient, the compound of formula (I) and the relevant therapeutic method.

In the Belgian Pat. No. 790,749, in the name of the assignee thereof, there is disclosed and claimed a series of derivatives of ammonium salts of the N-substituted anilinic acid, having the general formula:

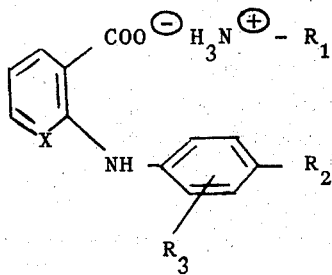

wherein
X is =CH— and —N=;
$R_1$ is an aliphatic radical containing at least a functional group selected from the alcoholic, the acidic and the basic group, and
$R_2$ and $R_3$ are —H, —CH$_3$, —CF$_3$, —Cl, —Br, —F, —CN, —SO$_2$NH$_2$.

Such derivatives are prepared by reaction in an appropriate solvent between an N-substituted anilinic acid having the formula:

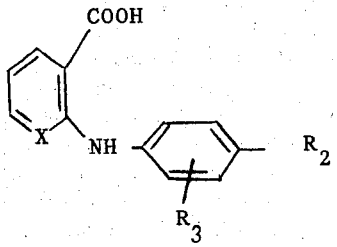

and a basic compound having the general formula:

wherein X, $R_1$, $R_2$ and $R_3$ have the previously specified meanings. In the above patent an anti-inflammatory activity is also indicated for these compounds.

The compound of formula (I), the subject-matter of the present invention, has shown, surprisingly, as the principal effect, a powerful analgesic action. To this action is associated, but only as a secondary feature, an anti-inflammatory action which is characteristic of the compounds of this class.

The compound (I) can be obtained by reaction of 2-anilino nicotinic acid (II) with lysine (III) (in the form of a base or a carbonate) in an appropriate medium, according to the following pattern:

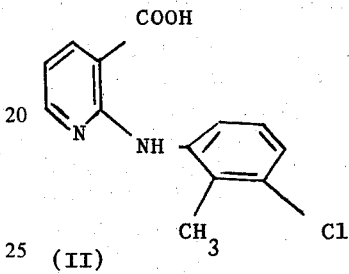

(II)

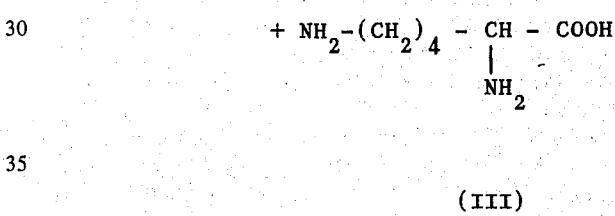

(III)

→

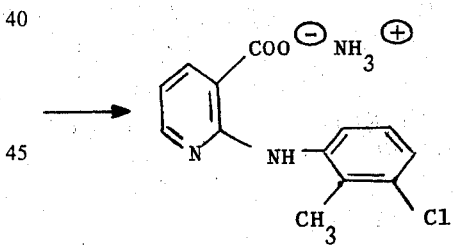

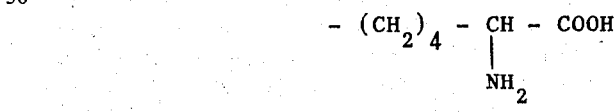

(I)

2-anilino nicotinic acid (II), in its turn, can be prepared by reacting the nitrile of a 2-halogennicotinic acid with 2-methyl-3-chloro aniline and subsequent hydrolysis of the thus obtained nitrile. This reaction can also possibly be carried out in the presence of organic solvents and with the possible presence of catalysts such as copper and/or potassium iodide.

The following examples have the purpose of illustrating, without however limiting, the preparation of the compound the subject of the present invention.

EXAMPLE 1

In a vessel having the appropriate volume there are admixed in 100 mls. anhydrous butanol, 0.2 mols of 2-chloronicotinonitrile, 0.2 mols of 2-methyl-3-chloro aniline and 0.5 grs. potassium iodide.

The mixture is refluxed during 3 hours, cooled and the excess butanol is distilled off. The residue which has been obtained is recrystallized from ethanol.

One obtains 2-(2-methyl-3-chloro-anilino)-3-cyano-piridine having a m.p. of 126° – 128°C.

0.2 mols of 2-(2-methyl-3-chloro-aniline)-3-cyano-piridine are dissolved in 300 mls. ethanol. The solution is supplemented with 100 grs. of an alkali metal hydroxide and 100 mls. water. The mixture is refluxed during 4 hours, the alcohol is distilled off and the residue is dissolved in water, the solution is filtered on carbon and with hydrochloric acid, the pH is adjusted to 2 so that a precipitate is formed, then the solution is allowed to cool and filtered.

One obtains 2-(2-methyl-3-chloro-anilino)-3-piridine carboxylic acid which, purified from isopropanol, melts at 233°–235°C.

6.8 grs. of 2-(2-methyl-3-chloro-anilino)-3-nicotinic acid are added to an aqueous solution of 10.8 mls. lysine (containing 37.3 grs. of lysine base). The pH is adjusted to 7.4 and water is distilled azeotropically with incremental additions of benzene. The product precipitates, is cooled and filtered and dried and there are obtained 10 grs. of lysine 2-(2-methyl-3-chloro-anilino)-3-nicotinate.

The analytical data of lysine 2-(2-methyl-3-chloro-anilino)-3-nicotinate are as follows:

```
mol.weight        408.88
m.p.              205°C–210°C (decomposition)
UV E₁ cm^1%       252 microns:   350–370
                  330 microns:   123–136
```

Thin layer chromatography with CF 254 silica-gel (solvent system: toluene, dioxan, acetic acid 90 : 25 : 1); $R_f$ = 0.32.

EXAMPLE 2

An appropriate vessel is charged with 150 mls. xylene and 0.2 mls. of 2-methyl-3-chloro aniline and the mixture is distilled until removing possible water traces. There are added 0.2 mols of 2-chloro-3-cyano piridine and the mixture is refluxed during 2 hours. The mixture is cooled and the excess xylene is distilled off, the residue is taken up with water and filtered. The product thus obtained is recrystallized from ethanol.

One obtains 2-(2-methyl-3-chloro-anilino)-3-cyano piridine which melts at 126°–128°C.

The procedure is then exactly as outlined in Example 1.

As already noticed, the product the subject of the present invention has proven to possess a powerful analgesic action which is improved over that of the conventional analgesics, both of the same class (2-anilino-(2'-methyl-3'-chloro)-nicotinic acid) and of chemical composition which is entirely different, such as acetylsalycilic acid and dextro propoxyphene hydrochloride.

Acute toxicity

The tests have been performed on mice and rats by the oral route and intravenously and have given the following results:

TABLE I

| Animal | Administration | DL50(°)mgms/kilogram b.w. |
|---|---|---|
| mouse | oral | 435 (306.34 – 617.70) |
| mouse | Intravenous | 170 (173.4 – 166.6 ) |
| rat | oral | 610 (732.0 – 508.33) |
| rat | Intravenous | 146 (137.73 – 154.76) |

(°)Calculated according to the method by Litchfield and Wilcoxon, J. Pharmacol., 1949, 96,99.

Subacute and chronic toxicities

The tests already completed on Wistar rats have shown the substantial absence of pathological alterations on the internal organs of the animals after administration which has lasted as long as 90 days of the compound (I) at three different daily dosages.

Analgesic action on mice

For this test, the contorsion method by Koster and co-workers (Fed. Proc., 1959, 18, 412) has been followed by using male and female mice weighing from 18 to 20 grams. The painful state was induced by peritoneally injecting 3%-acetic acid (0.25 ml. per animal).

The compound according to the present invention has been compared in this test with other known analgesics of common use, such as acetylsalicylic acid, dextropropoxyphene hydrochloride and 2-anilino-(2'-methyl-3'-chloro)-nicotinic acid.

In the following Table there have been tabulated the efficiency values, by attributing to acetylsalicylic acid the unitary reference value.

TABLE 2

| Compound | Analgesic efficiency |
|---|---|
| Acetylsalicylic acid | 1 |
| Novalgine | 0.7 |
| 2-(2-methyl-3-chloro-anilino)-nicotinic acid (CLONIXIN) | 5.85 |
| Dextro propoxyphene hydrochloride | 14.40 |
| Lysine 2-(2-methyl-3-chloro-anilino)-3 nicotinate | 23.6 |

The analgesic action has been also tested with the method by Grotto and Sulman, (Arch.Int.Pharmacodyn., 1967, 165, 152) by introducing the mouse tail in hot water. Also in this case the results of the comparison with the other known analgesic compounds confirm the results indicated above.

These and other results of the pharmacological tests have been positively confirmed by the clinical tests which have been subsequently carried out on humans.

The tests were carried out in "double blind" and to 60 patients (37 men and 23 women of age ranging from 18 to 71 years), divided into two groups of 30 patients, there were administered, respectively, 2-(2-methyl-3-chloro-anilino)-lysine nicotinate at the dosages of 125 milligrams in the form of tabloids and 100 milligrams in injectable form, and CLONIXIN which was administered by the oral route only at the dosage of 600 milligrams of the active principle.

The patients suffered from post-traumatic pains (from luxations and bone fractures), from post-operatory pains, from lomboscystalgia, dental pains, bowel cholics and others.

In the group treated with 100 milligrams of the compound (I) intramuscularly, the analgesic action was ascertainable after 5–10 minutes, and after 10–15 minutes in the patients treated by the oral route with 125 milligrams of the same compound.

The duration of the analgesic effect was 4 to 6 hours in the patients treated by the oral route and 3–5 hours in those subjected to injections.

In the following Table the analgesic effect is reported by way of summary:

TABLE 3

| Result | Compound I | | CLONIXIN |
|---|---|---|---|
| | Orally | Parentherally | Orally |
| excellent | 66% | 73% | 30% |
| good | 27% | 27% | 47% |
| regular | 7% | 0% | 23% |
| no effect | 0% | 0% | 0% |

During progress of these tests also the tolerability of the drug was tested and the secondary and side-effects were also investigated, which consisted in epigastric pains, dizziness, nausea, vomit and sweat. The results are tabulated in the following Table.

TABLE 4

| Result | Compound I | | CLONIXIN |
|---|---|---|---|
| | Orally 15–125 mgms | Parentherally 15–100 mgms | Orally 300–600 mgms |
| Tolerability | | | |
| excellent | 60% | 70% | 20% |
| very good | 33% | 30% | 37% |
| good | 7% | 0% | 23% |
| regular | 0% | 0% | 20% |
| side effects | 10% | 0% | 33% |

Apart from the foregoing, the pharmacological tests, such as those on the paw edema by carragenin and the inflammation as chronically induced by cotton pellets, have shown the presence of a good anti-inflammatory activity.

In conclusion, the compound according to the present invention has analgesic activity at dosages of from 10 to 500 milligrams, preferably 15 to 200 milligrams. More particularly, the optimum dosages for the individual administration routes are the following:

| 1) Tabloids | 125 milligrams per dose |
| 2) Injectable form | 100 milligrams per dose |
| 3) Suppositories | 200 milligrams per dose |

Obviously, in each case the active principle will be formulated with the methods and the substances as commonly used in the pharmaceutical art, such as they are well known to those skilled in the art.

Under the respect of the therapeutic method, the clinical tests have shown that optimum effects as analgesic are obtained with 3 to 4 daily administrations.

What is claimed is:

1. A method of inducing analgesia comprising administering an analgesic effective amount of a composition consisting essentially of a pharmaceutically acceptable carrier and an active principle, the active principle being 2-(2-methyl-3-chloro-anilino)-lysine nicotinate having the formula:

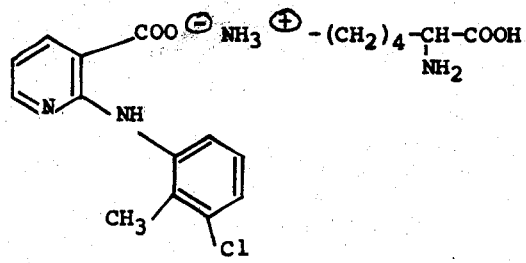

2. The method according to claim 1, wherein said active principle is present in a dosage from 10 to 500 milligrams.

3. The method according to claim 2, wherein said dosage is of 15 to 200 milligrams.

4. The method according to claim 1, wherein said composition is in the form of tabloids for oral administration, containing 125 milligrams of said active principle.

5. The method according to claim 1, wherein said composition is in the form of dosage units of injectable solution containing 100 milligrams of said active principle in a pharmaceutically acceptable liquid carrier.

6. The method according to claim 1, wherein said composition is in the form of suppositories containing 200 milligrams of said active principle.

* * * * *